United States Patent
Young et al.

(10) Patent No.: US 6,625,303 B1
(45) Date of Patent: Sep. 23, 2003

(54) METHOD FOR AUTOMATICALLY LOCATING AN IMAGE PATTERN IN DIGITAL IMAGES USING EIGENVECTOR ANALYSIS

(75) Inventors: Susan S. Young, Buffalo, NY (US); Hsien-Che Lee, Penfield, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/501,334

(22) Filed: Feb. 9, 2000

Related U.S. Application Data

(63) Continuation-in-part of application No. 09/243,400, filed on Feb. 1, 1999, now Pat. No. 6,249,590.

(51) Int. Cl.$^7$ ................................................. G06K 9/00

(52) U.S. Cl. ......................... 382/132; 382/199; 382/224

(58) Field of Search .................................. 382/128, 107, 382/131, 132, 190, 224, 199; 348/169

(56) References Cited

U.S. PATENT DOCUMENTS

| | | | |
|---|---|---|---|
| 4,851,984 A | | 7/1989 | Doi et al. |
| 4,922,915 A | | 5/1990 | Arnold et al. |
| 4,951,201 A | | 8/1990 | Takeo et al. |
| 5,228,068 A | | 7/1993 | Mazess |
| 5,311,600 A | * | 5/1994 | Aghajan et al. ............ 382/156 |
| 5,602,935 A | * | 2/1997 | Yoshida et al. ............. 382/132 |
| 5,633,511 A | | 5/1997 | Lee et al. |
| 5,673,298 A | * | 9/1997 | Mazess ......................... 378/54 |
| 5,696,805 A | * | 12/1997 | Gaborski et al. ............. 378/54 |
| 6,363,163 B1 | * | 3/2002 | Xu et al. ...................... 382/130 |
| 6,408,109 B1 | * | 6/2002 | Silver et al. ................. 382/300 |

OTHER PUBLICATIONS

EXM Eigen Templates for Detecting and Classifying Arbitrary Junctions by Dibyendu Nandy et al. IEEE 1998.*

Journal of Bone and Mineral Research, vol. 12., Supplement 1, Aug. 1997, pp. S508, A New Region of Interest in the Forearm for Monitoring Effect of Therapy by, C. Christiansen, P. Ravn, P. Alexandersen, and A. Mollgaard.

1994 Butterworth–Heinemann Ltd, Image and Vision Computing vol. 12, No. 4, May 1994, Segmentation of the finger bones as a prerequisite for the determination of bone age, by: D.T. Morris and C.F. Walshaw, pp. 239–245.

IEEE Transactions on Medical Imaging, vol. 12, No. 1, Mar. 1993, Feature Extraction in Carpal–Bone Analysis, by: W. Pietka, L. Kaabi, M.L. Kuo, H.K. Huang, pp. 44–49.

IEEE Transactions on Medical Imaging, vol. 10, No. 4, Dec. 1991, Computer–Assisted Phalangeal Analysis in Skeletal Age Assessment, by: E. Pietka, M.F. McNitt–Gray, M.L. Kuo, H.K. Huang, pp. 616–620.

(List continued on next page.)

*Primary Examiner*—Jon Chang
*Assistant Examiner*—Chong Kim
(74) *Attorney, Agent, or Firm*—William F. Noval

(57) ABSTRACT

A method for automatically locating instances of a specified image structure in digital images, comprising the steps of: providing a digital image; detecting simple features associated with the specified image structure in the digital image; for each detected feature, searching, in its spatial neighborhood, for a second or a plural of other features associated with the specified image structure; for each pair of plural of features detected, using an eigenvector classifier to distinguish the wanted features and the unwanted features by matching the eigenvector representation that is constructed from a set of training profiles; and labeling those image regions that are found to be consistent with the specified image structure in the classifying step.

4 Claims, 22 Drawing Sheets

OTHER PUBLICATIONS

Med. Phys. 20 (4), Jul./Aug. 1993, Computer–Aided Diagnosis: Detections and Characterization of hyperparathyroidism in Digital Hand Radiographs, by: L. Chang, H. Chan, L. Niklason, M. Cobby, J. Crabbe, R. Adler, pp. 983–992.

Computers and Geosciences vol. 19, No. 3, pp. 303–342, 1993, Principal Components Analysis (PCA), by: Andrzek Mackiewicz and Waldemar Ratajczak.

Optical Society of America, vol. 4, No. 3, Mar. 1987, Low–Dimensional Procedure For The Characterization of Human Faces, by: L. Sirovich and M. Kirby, pp. 519–524.

IEEE Transactions of Pattern Analysis and Machine Intellegence, vol. 19, No. 7, Jul. 1997, Eigenfaces vs. Fisherfaces: Recognition Using Class Specific Linear Projection, by: Peter Belhumeur, Joao Hespanha, and David Kreigman, pp. 711–720.

Proceedings of the IEEE, vol. 85, No. 9, Sep. 1997, Face Recognition: Eigenface, Elastic Matiching, and Neural Nets, by: J. Zhang, Y. Yan, M. Lades, pp. 1423–1435.

* cited by examiner

METHOD FOR AUTOMATICALLY LOCATING AN IMAGE PATTERN IN DIGITAL IMAGES USING EIGENVECTOR ANALYSIS

CROSS-REFERENCE TO RELATED MATERIALS

This application is a Continuation-In-Part of U.S. patent application Ser. No. 09/243,400, filed Feb. 1, 1999, entitled METHOD FOR AUTOMATICALLY LOCATING AN IMAGE PATTERN IN DIGITAL IMAGES, inventors Young and Lee, now U.S. Pat. No. 6,249,590.

FIELD OF THE INVENTION

This invention relates in general to a method for automatically locating instances of a specified image pattern in a digital image, and more specifically relates to a method for the automatic detection and classification of cylindrical bone patterns in digital projection radiographs.

BACKGROUND OF THE INVENTION

Image processing algorithms that can automatically detect and classify patterns in digital imagery have broad application in consumer photography, remote sensing, and medical imaging. The present invention describes a flexible and computationally efficient approach for detecting and classifying patterns in digital imagery that has specific application to digital projection radiography. The method is useful for image visualization processing and computer aided diagnosis (CAD). The present invention has been optimized for the detection and classification of cylindrical bone patterns in digital projection radiographs.

Finding the location of the anatomical region-of-interest (ROI) in a digital projection radiograph is a critical step for enhancing the brightness, contrast and sharpness of an image. Once the ROI has been identified, standard techniques such as tone scaling and unsharp masking can be used to optimally render the image for diagnostic interpretation. The automatic segmentation of the bone and soft tissue anatomical regions is especially useful for generating image renderings that maximize the diagnostic information content that is presented to the radiologist for various types of exams. This processing must be fully automated to facilitate workflow in busy hospital imaging departments. Automatic detection of patterns in digital radiographs also has application to CAD. For example the automatic identification of certain bone patterns can be used as a pre-processing step for computer-assisted image interpretation. Once a specific bone pattern has been located, the bone morphology can be analyzed to obtain information about bone mineral density, bone growth, and fractures. The present invention has been optimized for locating the class of "cylindrical" bones, e.g. the humerus, femur, fingers, ribs, etc. However the technique is very flexible and may be generally applied to the detection of patterns in other image types such as for the automatic detection of cancerous masses and microcalcifications in mammography. The technique is especially useful for higher dimensional spatial or spectral imagery, e.g., 3-dimensional CT or dual energy x-ray capture. In these applications, simple features can be used to first locate candidate regions which are then examined and classified by more detailed analysis.

Measurements of bone density have become an essential criterion for evaluating a patient's risk of osteoporostic fracture. Commercially available instruments for measuring the bone mineral density (BMD) are divided into X-ray absorptiometry, quantitative computed tomography (QCT), and quantitative ultrasound (QUS). QCT allows the 3D visualization of trabecular microstructure and provides assessments beyond the basic BMD result, such as biomechanical parameters describing bone strength. However, QCT requires a CT scan and is an expensive procedure. Dual-energy X-ray absorptiometry (DXA) of the spine, femur, and total-body is a widely utilized method for predicting a patient's risk of fracture. However, in many geographic areas there are inadequate resources to meet the demand, and DXA scans are not available to all patients who might benefit. Moreover, conventional DXA scanning is perceived as costly because of the need to refer patients to hospital-based facilities. Recently, there has been a wide variety of innovative equipment available for a small, low-cost dual-energy X-ray absorptiometry device dedicated to scanning the peripheral skeleton, for example, the forearm. As discussed in Christiansen et al. (C. Christiansen, P. Ravn, P. Alexandersen, and A. Mollgaard, "A new region of interest (nROI) in the forearm for monitoring the effect of therapy," Journal of Bone Mineral Research, 12 (suppl 1): S480, 1997.), BMD measurements at forearm sites are well proven in predicting fracture risk. There is also a single-energy X-ray device, called radiographic absorptiometry (RA), where BMD in the hand (that is, the fingers) is assessed using a radiograph calibrated with an aluminum wedge. In the most recent development, devices designed to acquire a direct digital radiographic image of the hand enable bone density analysis to be performed in a physician's office.

The challenge for computer aided diagnosis of bone disease is to position the region of interest for a highly precise measurement of BMD. Various methods for locating the bone region of interest have been proposed. For example, in order to use a posterior/anterior (PA) chest radiograph to analyze lung texture, the inter-rib bones shown in the PA chest image need to be removed. U.S. Pat. No. 4,851,984, "Method and system for localization of inter-rib spaces and automated lung texture analysis in digital chest radiographs", issued Jul. 25, 1989, to inventors K. Doi, et al., teaches a method to locate inter-rib spaces in digital chest radiograph images. First, a lung field is defined by determining the rib cage edge boundary. A horizontal signal profile is obtained at a predetermined vertical location. The pixel location at which the second derivative of this horizontal profile is minimum is defined as the rib cage edge boundary. Then two vertical profiles in the periphery of both lungs are fitted with a shift-invariant sinusoidal function. This technique assumes that the horizontal line is always perpendicular to the spinal column. Moreover, it assumes that the relative vertical locations of the objects are known a priori. Therefore, U.S. Pat. No. 4,851,984 does not teach a fully automatic method for locating instances of an image pattern. Furthermore, the profiles of the sinusoidal function do not accurately fit the profile of the cylindrical bone structure.

Histogram methods have been used to locate the bone region of interest. U.S. Pat. No. 5,228,068, "Device and method for automated determination and analysis of bone density and vertebral morphology", issued Jul. 13, 1993, to inventor R. B. Mazess, teaches a method to determine and analyze vertebral morphology by evaluating the approximate center location of each vertebra from a digital lateral vertebral scan. The centers are located by evaluating the horizontal and vertical histograms. The horizontal histogram is constructed along a line which crosses each anterior-posterior border of the vertebra. The vertical histogram is obtained along a line crossing the superior-inferior border, which directs the spine column, because the patient is supported in the supine position on a table so that the vertebrae of the spine are generally aligned with the scan direction. However, because of the curvature of the spine, the angle of the vertebrae, that is, the angle of the anterior border, the posterior border, the superior border, and the inferior border with respect to the scan direction will vary among vertebrae. This method requires that this variation be accommodated by the trained eye of a physician in estimating the initial positions of lines which horizontal and vertical histogram are generated from. The rigid assumption about the relative orientation of the image relative to the body makes this technique sensitive to orientation error and can not be used in automatic mode for general image orientations.

Another histogram-based method disclosed in U.S. Pat. No. 4,951,201, issued Aug. 21, 1990, "Method of automatically determining imaged body posture in medical image display", to inventors H. Takeo et al, is used to determine the image body posture. In order to produce an optimal visualization of the anatomy, the projection must be known. For example, for a chest image, the imaged thoracic vertebrae is of a relatively low density when it is imaged from the front side, and of relatively high density when it is imaged from the lateral side. This method determines imaged body posture by analyzing the histogram characteristics along a prescribed direction across the image. However, the method does not describe whether a prescribed direction is determined by a user interaction or by an automatic algorithm.

Other methods have used shape information to locate the bone region of interest. U.S. Pat. No. 4,922,915, "Automated image detail localization method", issued May 8, 1990 to inventor B. A. Arnold, teaches a method to place a regular (e.g., elliptical) or irregular shape in a specific region of the image of the patient's anatomy, such as the trabecular bone region of the patient's spine. The cross-section image of an upper region of vertebra body contains the cortical bone image that appears as an outer ring, the trabecular bone image which occupies a portion of inside the ring, and the basivertebral vein image which occupies another small portion inside the ring. It is desired to exclude the basivertebrae vein from the trabecular bone image. This method requires that the operator position the enlarged region of interest so that it encompasses the top region of the vertebral body including the trabecular bone image but excluding the basivertebral vein image. Then the template search and histogram analysis algorithms are used to place the trabecular bone region.

Some researchers have proposed methods to segment images of the hand bone for the purpose of age assessment (see: e.g., (1) D. T. Morris and C. F. Walshaw, "Segmentation of the finger bones as a prerequisite for the determination of bone age," Image and Vision Computing, Vol. 12, No. 4, pp. 239–246, May 1994; (2) E. Pietka, L. Kaabi, M. L. Kuo, and H. K. Huang, "Feature extraction in carpal-bone analysis," IEEE Transactions on Medical Imaging, Vol. 12, No. 1, pp. 44–49, 1994; (3) E. Pietka, M. F. McNitt-Gray, M. L. Kuo, and H. K. Huang, "Computer-assisted phalangeal analysis in skeletal age assessment," IEEE Transactions on Medical Imaging, Vol. 10, No. 4, pp. 616–619, December 1991 ;(4) C.-L. Chang, H.-P. Chan, L. T. Niklason, M. Cobby, J. Crabbe, and R. S. Adler, "Computer-aided diagnosis: detection and characterization of hyperparathyroidism in digital hand radiographs," Medical Physics, 20(4), pp. 983–992, July/August 1993), and of the femur bone for the calculation of bone growth (see: U.S. Pat. No. 5,673,298, "Device and method for analysis of bone morphology", issued Sep. 30, 1997, to inventor R. R. Mazess). In publications (1), (2) and (3) and in Mazess's patent, the hand bone and the femur bone regions of interest were defined using a standard thresholding technique to separate the hand or femur from the background. Unfortunately, thresholding is not a robust and reliable image segmentation method for the texture-rich digital projection radiographic images. In Chang et al.'s publication (4), the extraction of the hand region of interest was performed manually. Then, an edge filter was applied to extract the edges of the finger bones. However, an edge filter usually produces numerous false alarms and misses, a complicated post-processing procedure is needed to remove these false alarms. The proposed method also relies on a human intervention, which is not desirable.

Eigenvector analysis, also known as principle component analysis, is a powerful statistical pattern classification method (see: K. Fukunaga, Introduction To Statistical Pattern Recognition, Academic Press, Inc., 1990; A. Mackiewicz and W. Ratajczak, "Principal components analysis (PCA)," Computers & Geosciences, Vol. 19, No. 3, pp. 303–342, March 1993.). The Eigenvector analysis method is a process of mapping the original measurements (e.g., the image space) into more effective features (e.g., a lower dimensional feature space), where the scatter of all mapped samples is maximized. Then, a classification criterion is designed based on a scatter measurement of the mapped coefficients. There are many applications of eigenvector analysis in the literature. The recent application of eigenvector methods to image analysis is found in face recognition (see: J. Zhang, Y. Yan, and M. Lades, "Face recognition: eigenface, elastic matching and neural nets," Proceedings of the IEEE, Vol. 85, No. 9, pp. 1423–1435, September 1997; P. N. Belhuneur, J. P. Hespanha, and D. J. Kriegman, "Eigenfaces vs. fisherfaces: recognition using class specific linear projection," IEEE Transactions on Pattern Analysis and Machine Intelligence, Vol. 19, No. 7, pp. 711–720, July 1997; L. Sirovitch and M. Kirby, "Low-dimensional procedure for the characterization of human faces," J. Optical Soc. of Am. A, vol. 2, pp. 519–524, 1987.). The eigenvectors of a covariance matrix of face vectors are generated to represent faces. Since the eigenvectors associated with the first few largest eigenvalues have face-like images, they also are referred to as eigenfaces. Finding the eigenvectors of the covariance matrix of an original image is difficult even for images of moderate size.

It is therefore desirable to provide a method which is simple, efficient and cost effective to solve these problems of known methods.

SUMMARY OF THE INVENTION

The present invention discloses a method for automatically locating instances of a specified pattern in a digital image using eigenvector analysis which solves the problems of known methods.

In general, the method effects extraction of certain image features first and then calculating the eigenvectors from this intermediate image feature space. According to a feature of the present invention there is provided a method comprising of providing a digital image from which simple features are detected that are associated with the specified pattern in the digital image. For each detected feature, a search is conducted in the spatial neighborhood of the detected feature for a second or a plural of other features associated with the target pattern. For each pair or plural of features detected, an eigenvector classifier is used to distinguish the wanted features from the unwanted features by matching the detected feature with the eigenvector representation that is constructed from a set of training profiles. The final step of the method is to label the image regions that are found to be consistent with the pattern in the classifying step.

ADVANTAGEOUS EFFECT OF THE INVENTION

The invention has the following advantages.

1. Specified image patterns are automatically located in digital imagery.
2. The eigenvector method reduces the dimensionality of multi-attribute feature sets, multi-band, and images that have high spatial dimensionality, thereby reducing computational complexity and improving signal to noise ratio.

Optimal automatic rendering of an image to highlight for interpretation a specified region of interest or image pattern in a digital image is facilitated.

Computer assisted diagnosis, which requires image segmentation and bone morphology analysis in a digital medical image is facilitated.

DETAILED DESCRIPTION OF THE INVENTION

The present invention discloses a general method for automatically locating instances of a specified image pattern in a digital image. In particular, this invention discloses a robust and computationally efficient method for automatically locating cylindrical bones in digital projection radiographs. The method is based on image pattern filters and eigenvector analysis. The characteristic profile (i.e., the code values on a line segment that crosses the bone perpendicular to the bone edge) of a cylindrical bone is selected as the basis for creating an image pattern. The characteristic profile for a cylindrical bone is generally comprised of two peaks corresponding to the high-density bone edge areas and of a valley corresponding to the less dense center region of the bone. The algorithm utilizes a gradient-based edge detection to locate candidate bone edge pixels. For each candidate pixel, the bone image profile is analyzed to identify indicators of bone location. Then, shape constraints of the image profile is used to refine the further selection of candidate profiles. A set of training profiles is used to construct an eigenvector representation for the characteristic cylindrical bone profiles. The algorithm then uses an eigenvector classifier to locate cylindrical bones in the imagery that match the eigenvector representation of the characteristic profile.

In the following description, the method of the invention will be described for locating cylindrical bones.

Figure 10:
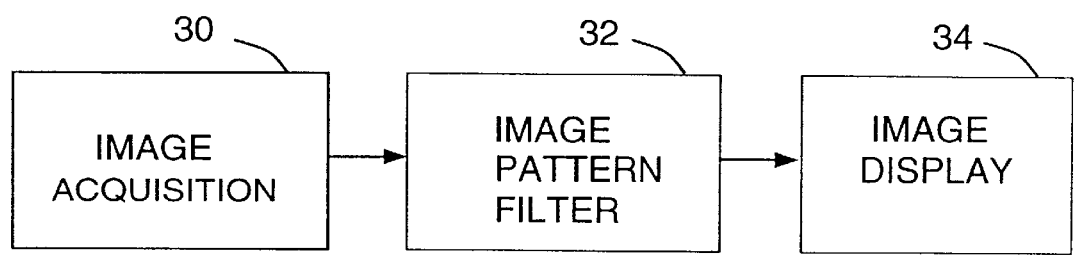
FIG. 10 is a block diagram of a digital image system incorporating the present invention.

Referring now to FIG. 10, there is shown a digital image system incorporating the present invention the digital image is acquired by image acquisition system 30. The digital image is processed by image pattern filter system 32 and the processed image is output to image display 34. Image acquisition system 30 can be one of the following: a computed radiography system; direct digital radiography system; radiographic film digitizer; diagnostic image modality (CT, MRI, US, NM, and PET); digital image archive. The image display can be a soft copy display (CRT, liquid crystal display) or a hard copy (film, paper).

Figure 9:
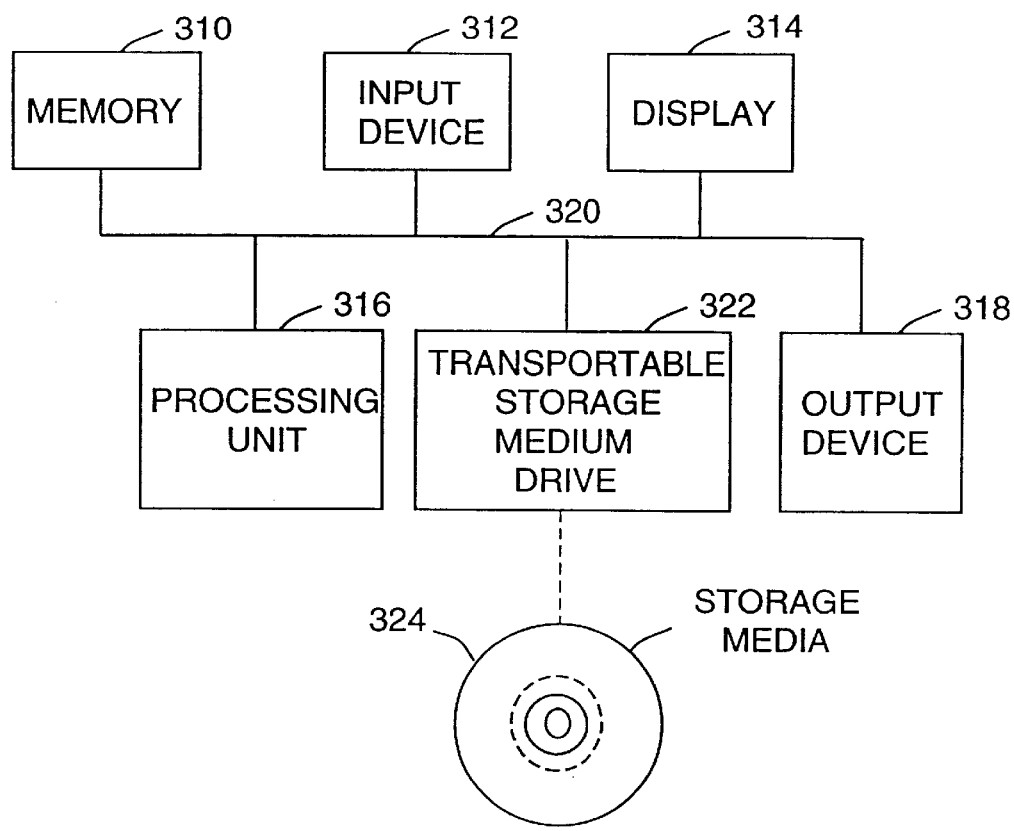
FIG. 9 is a block diagram of a digital image processing system for carrying out the present invention.

The digital image is processed in image pattern filter system 32 (FIG. 10) according to the method of the present invention. System 32 can take the form of a digital computer, such as illustrated in FIG. 9. In such case, one or more of the steps of said method can be carried out using software routines. Image processor can also include hardware or firmware for carrying out one or more of the method steps. Thus, the steps of the method of the invention can be carried out using software, firmware, hardware either alone or in any preferable combination.

As shown in FIG. 9, a digital computer 300 includes a memory 310 for storing digital images, application programs, operating system, etc. Memory 310 can include mass memory (such as a hard magnetic disc or CD ROM), and fast memory (such as RAM). Computer 300 also includes input device 312 (such as a keyboard, mouse, touch screen), display 314 (CRT monitor, LCD), central processing unit 316 (microprocessor), output device 318 (thermal printer, dot matrix printer, laser printer, ink jet printer). Components 310, 312, 314, 316, 318 are connected together by control/data bus 320. Computer 300 can include a transportable storage medium drive 322 for reading from and/or writing to transportable storage media 324, such as a floppy magnetic disk or write-able optical compact disk (CD). As used in this application, computer readable storage medium can include, specifically, memory 310 and transportable storage medium 324. More generally, computer storage medium may comprise, for example, magnetic storage media, such as magnetic disk (hard drive, floppy disk) or magnetic tape; optical storage media, such as optical disk, optical tape, or machine readable bar code; solid state electronic storage devices, such as random access memory (RAM), read only memory (ROM); or any other physical device or medium which can be employed to store a computer program. Following is the method of the invention as applied to finding cylindrical bone patterns and the major steps of locating cylindrical bones.

Figure 1A:
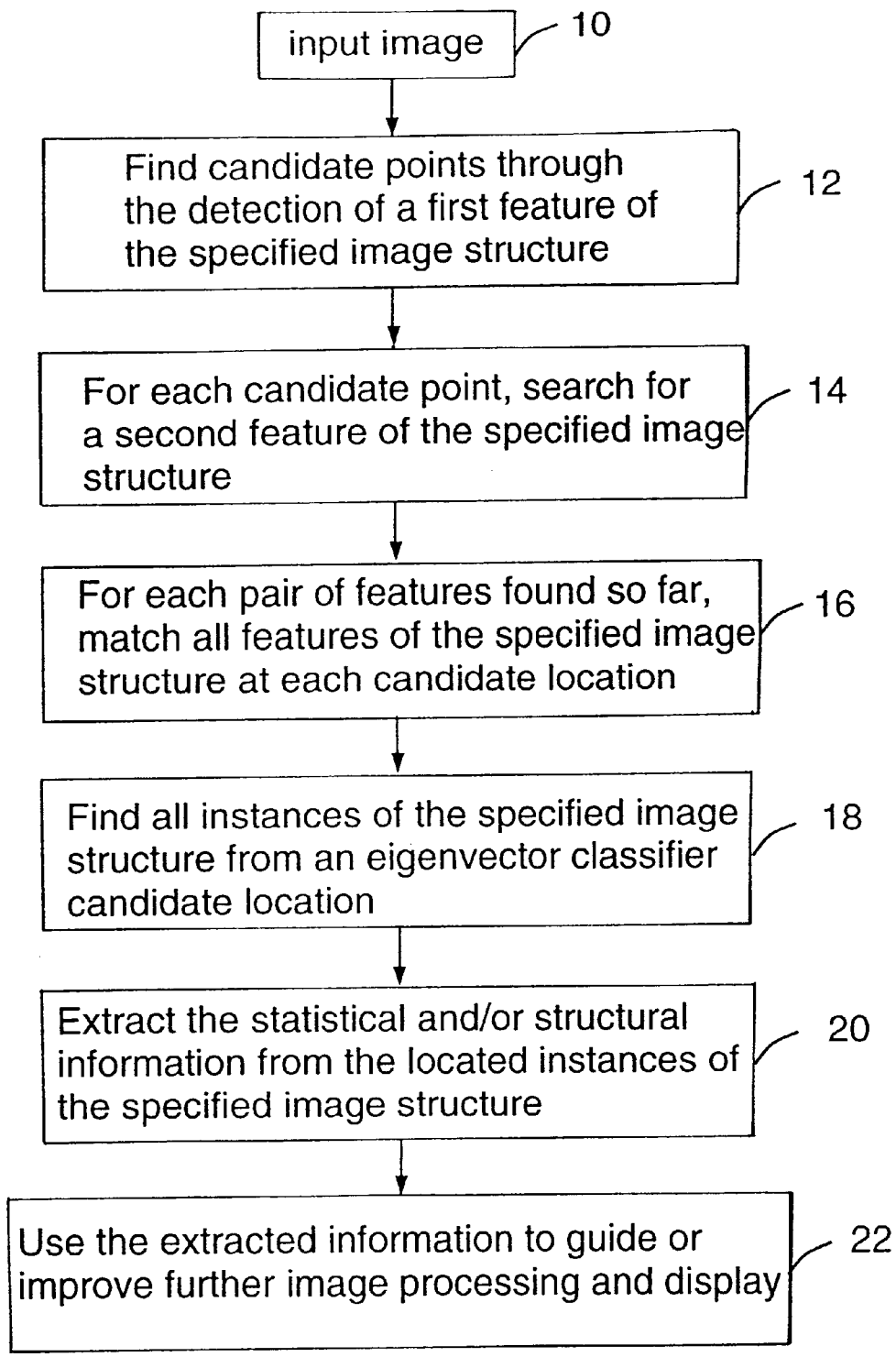
FIG. 1(a) is a block diagram showing the general method of the present invention for automatically locating instances of a specified image pattern in a digital image.

Referring now to FIG. 1a, there is shown a flow diagram of the general method of the present invention for automatically locating instances of a specified image pattern in a digital image. A digital image is input (box 10). Then, candidate points are found through the detection of a first feature of the specified image pattern (box 12). For each candidate point, a search is conducted for a second feature of the specified image pattern (box 14). For each pair of features found so far, all features of the specified image pattern are matched at each candidate location (box 16). Next, all instances of the specified image pattern are obtained from an eigenvector classifier (box 18). Then, the statistical and/or structural information is extracted from the located instances of the specified image pattern (box 20). Last, the extracted information is used to guide or improve further image processing and display (box 22).

Figure 1B:
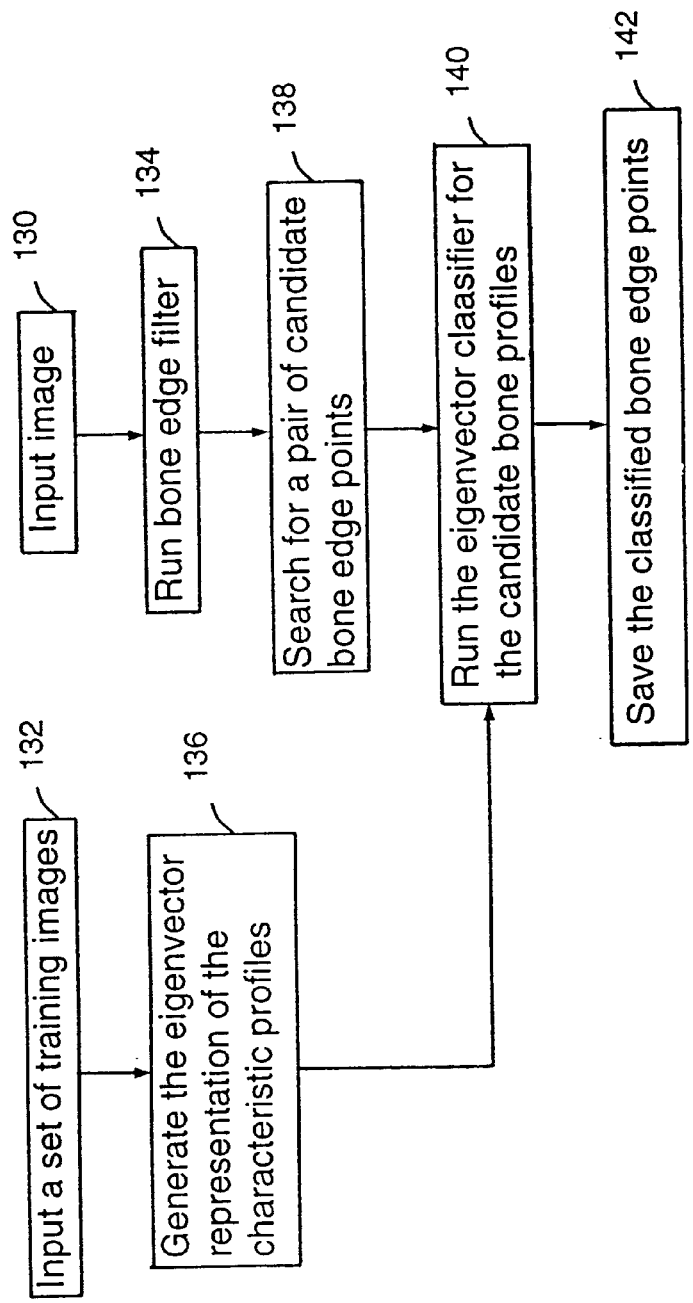
FIG. 1(b) is a block diagram of the present invention as applied to the problem of automatically locating the cylindrical bone pattern from a digital projection radiograph.

FIG. 1b is a flow diagram of the method of the present invention as applied to the problem of automatically locating the cylindrical bone pattern structure from the digital projection radiographic images. A digital image and a set of training images are provided (box 130 and box 132). The eigenvector representation algorithm is run on the set of training digital images (box 136). A bone edge filter is run on the input digital image (box 134). Then, a search is conducted for pairs of bone edge points (box 138). The candidate bone profiles between the pair of bone edge points are sent to the eigenvector classifier (box 140). Lastly, the classified bone points are saved for further image processing and display (box 142).

Cylindrical Bone Pattern

For example, consider the humerus (upper arm bone). A line segment is analyzed which crosses the humerus. The image profile (i.e., the code values of the image along this line) is presented in FIG. 2. This image profile represents the gray level transitions along the line crossing the bone. The humerus has a lower density in the middle region, which is called humeral shaft, and has a higher density at its two edge regions. The two peaks of the bone image profile in FIG. 2 correspond to the middle points of the two highest density bone edge regions. The valley area between the two peaks corresponds to the lower density shaft area. The maximum and minimum gradient points of the image profile represent the points separating the bone from the soft tissue surrounding it. The maximum gradient point is called the left maximum gradient point, or the left edge point, and the minimum gradient point is called the right maximum gradient point, or the right edge point. For example, in FIG. 2, the left maximum gradient point A is located at distance 8 and the right maximum gradient point B is at distance 25.

Figure 2:
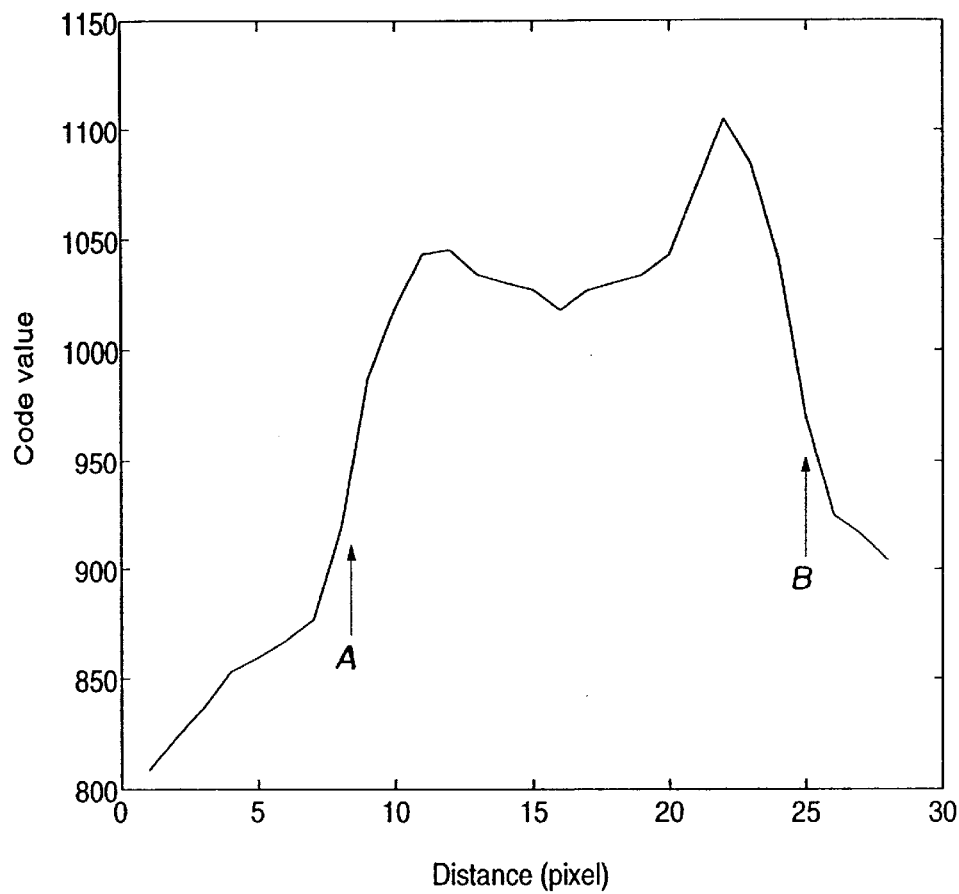
FIG. 2 is a graphical view showing the image profile of a line crossing a humerus. The two peaks of this image profile correspond to the middle points of the two highest density bone edge regions, while the valley corresponds to the less dense center region of the bone. The two positions pointed to by the two arrows correspond to the maximum and minimum gradient points of the profile and represent the points separating the bone from the soft tissue.

The image profile shown in FIG. 2 represents the profile of the image with inverse polarity. Greater code values represent the brighter areas of the image and the lower code values represent the darker areas. The image profile of a cylindrical bone is comprised of the transition of the gray levels of the bone to the surrounding anatomy. The unique "two-peak" shape of the image profile and the bone edge points are used as the "cylindrical bone pattern". An eigenvector-based cylindrical bone pattern classification method is described in the following section. However, this invention can be applied to the detection of any pattern in a digital image, either radiographic or non-radiographic.

Locating Cylindrical Bones (1) Eigenvector Analysis

An image profile consists of n samples along the line crossing the bone. The image profile, call it X, is an n-dimensional random vector. Using orthogonal decomposition of vectors (Fukunaga, 1990), the vector X can be represented without any error via the summation of n linearly independent (orthogonal) basis vectors as shown in the following:

$$X = \sum_{i=1}^{n} y_i \Phi_i = \Phi Y, \tag{1}$$

where $$\Phi=[\Phi_1, \ldots, \Phi_n], Y=[y_1, \ldots, y_n]^T,$$

and $$\Phi_i=[\Phi_{i1}, \ldots, \Phi_{in}]^T, i=1, \ldots, n.$$

The $\Phi$ is made up of n linearly independent column vectors. An objective of eigenvector analysis is to reduce the dimensionality of the signal subspace $\Phi$, which results in reduced computational load and improved Signal-to-Noise Ratio (SNR).

The following operation removes the basis vectors that contain a small portion of the energy of X. For this purpose, choose only m where m≦n of the basis vectors $\Phi$'s in equation (1) to approximate X accurately. Without loss of generality, assume that only the first m basis vectors are selected. Then, the above-mentioned approximation of X can be expressed via the following:

$$\hat{X} = \sum_{i=1}^{m} y_i \Phi_i = \Phi(m)Y(m), \quad (2)$$

where $$\Phi(m)=[\Phi_1, \ldots, \Phi_m].$$

The mean-square error of the resulting approximation can be written via $$\bar{\varepsilon}^2(m) = \sum_{i=m+1}^{n} |y_i|^2.$$

It can be shown (Fukunaga, 1990) that the optimum choice for the $\Phi$'s, which minimizes the mean-square error $\bar{\varepsilon}^2(m)$, is the eigenvectors of the covariance matrix of X, that is, $$C_X \Phi_i = \lambda_i \Phi_i,$$

where $C_X$ is the covariance matrix of X, and $\lambda_i$ is the eigenvalue that is associated with the eigenvector $\Phi$. In this case, the minimum mean-square error becomes $$\bar{\varepsilon}^2(m)_{opt} = \sum_{i=m+1}^{n} \lambda_i.$$

(2) Eigenvector Representation of Cylindrical Bone Profiles

In order to extract the eigenvector representation of bone profiles, select a set of bone profiles as the training bone set. The automatic method of extracting a bone profile is presented in Section (5), Bone Pattern segmentation. The following shows the method of constructing an approximation of the bone profile via eigenvector decomposition.

1. Select a set of k training bone image profiles:

$$P=[P_1, \ldots, P_k]^T, \quad (3)$$

where $P_j$, j=1, . . . , k, is a row vector representing the j th bone profile that consists of n sample points, that is, $$P_j=[p_1, \ldots, n], j=1, \ldots, k. \quad (4)$$

2. Calculate the covariance matrix of P:

$$C_P = \frac{1}{k-1}\sum_{j=1}^{k} [P_j - \mu_P]^T [P_j - \mu_P],$$

where $$\mu_P = \frac{1}{k}\sum_{j=1}^{k} P_j$$

is the n dimensional mean profile vector of P.

3. Solve the eigenvector matrix $\Phi$ and eigenvalue matrix $\Lambda$ of the covariance matrix $C_P$ using the singular value decomposition method, such that $$C_P\Phi=\Phi\Lambda,$$

where $$\Phi=\Phi[_1, \ldots, \Phi_n]$$

and $\Lambda$ is a diagonal matrix with eigenvalues as its elements, that is, $$\Lambda=\text{diag}(\lambda_1, \ldots, \lambda_n).$$

4. Choose m basis vectors that contain a large portion of the energy of the training data, that is, $$\sum_{i=1}^{m} \lambda_i \geq \alpha \sum_{i=1}^{n} \lambda_i,$$

where the constant $\alpha$ can be selected to be very close to 100%, such as 99% or 98%.

5. Project the vector $P_j$ onto the selected m basis vectors via $$a_{ji}=<P_j^T, \Phi_i>,$$

where $a_{ji}$ is called the projection coefficient, i=1, . . . , m, j=1, . . . , k, and <x,y> represents the inner product of x and y.

6. Construct the approximation of $P_j$ via $$\hat{P}_j = \sum_{i=1}^{m} a_{ji}\Phi_i^T(m) = A_j(m)\Phi^T(m), j = 1, \ldots, k$$

where $$A_j(m)=[a_{j1}, \ldots, a_{jm}]$$

is called the projection coefficient vector.

7. Construct the approximation of P via $$\hat{P}=A(m)\Phi^T(m),$$

where A(m) is called the projection coefficient matrix, that is, $$A(m)=[A_1(m), \ldots, A_k(m)]^T.$$

(3) Scatter Measurement

A classifier was designed to distinguish between the bone structures and the non-bone structures based on a metric referred to as the scatter measure that is discussed next. Let $\mu_A$ and $C_A$ be the mean vector and the covariance matrix of the projection coefficient matrix A(m) from a training set of the bone profiles, respectively. The scatter measurement is the distance between the projection coefficient vector $A_t(m)$ of a test image profile $P_t$ and the projection coefficient matrix of the training bone set, that is, $$d = (A_t(m) - \mu_A)^T C_A^{-1} (A_t(m) - \mu_A). \quad (5)$$

If $d < \delta$, the test image profile is classified as a bone profile; otherwise, it is not. The parameter $\delta$ is typically chosen to be around 3, this represents an acceptable bone profile distribution within 3 standard deviations of the training data.

(4) Bone Profile Registration

Figure 3:
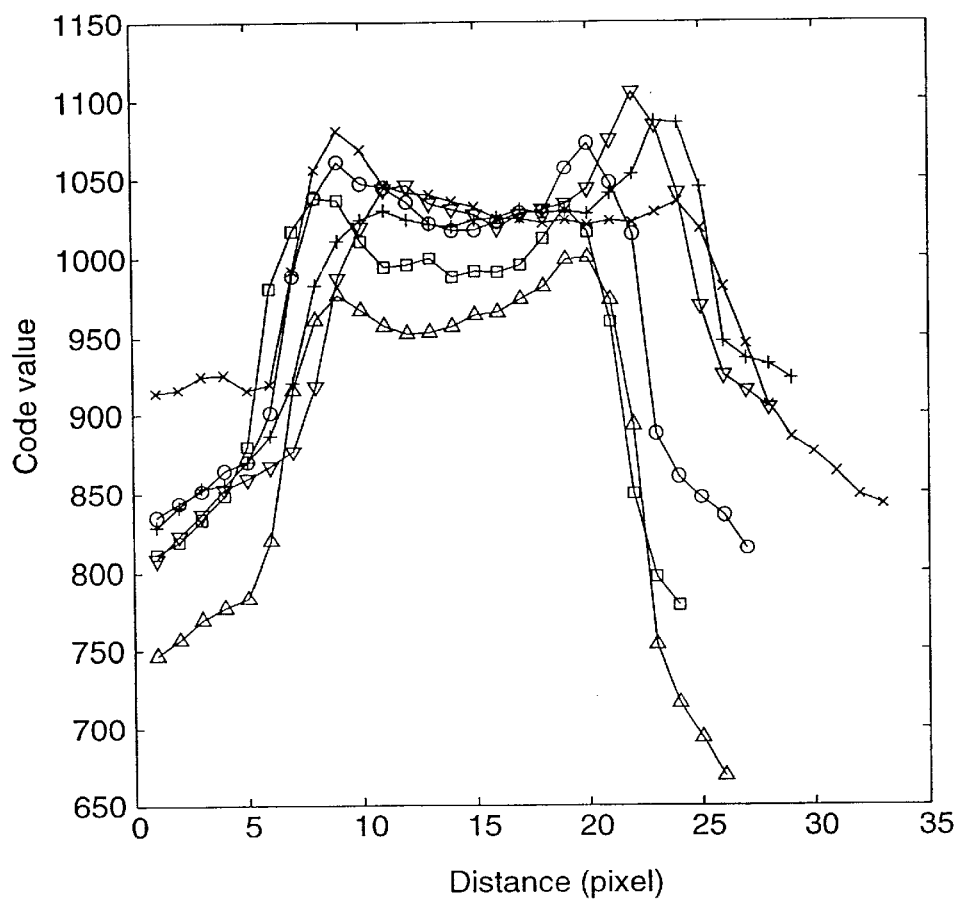
FIG. 3 is a graphical view showing six image profiles from a humerus. They are not properly aligned when they are plotted in the same coordinate system.

The shape of the cylindrical bone image profile is unique as shown in FIG. 2. However, the bone image profiles that are obtained from different line segments of different cylindrical bones, even when they are selected from a single bone, are not properly aligned when they are plotted in the same coordinate system. FIG. 3 shows six bone profiles from a humerus. It can be observed from this figure that these image profiles exhibit different locations of the maximum and minimum gradient points (i.e., the two edge points), different DC code values (gray levels), and a different number of points between the two edge points. This is attributed to different x-ray exposure energies scattered in different directions on the bone during the image formation process, and due to variations in the width of the bone.

In order to analyze image profiles on a common coordinate system, the profiles must be registered such that they align on the same maximum and minimum gradient points (i.e., the two edge points), align on a common DC value, and have the same number of sample points between the two edge points. One image profile was selected as the basis profile.

The other image profiles were then registered based on this basis profile the following procedure describes how to register two image profiles. To register multiple image profiles, repeat the procedure.

1. Horizontal registering

Register the two image profiles so that the left and right edge points are aligned. This step is called horizontal registering. First align the second profile to the first profile on the left maximum gradient point (left edge point), then scale the second profile such that the right edge points of the two profiles are aligned.

2. Vertical registering

Next register the two profiles such that they have a common DC value. This step is called vertical registering. A constant value must be added to the second profile for this purpose. This constant value is the difference between the vertical values of the two profiles. The vertical value of a profile is calculated as the average code value of the central 5 points.

3. Interpolating

After the two profiles are aligned horizontally and vertically, cubic spline interpolation is used to force the two profiles to have the same number of points between the two edge points.

(5) Bone Pattern Segmentation

This section describes a method for automatically extracting bone edge points and bone image profiles by segmenting the bone patterns. This automatic bone profile extraction method can be applied to extract both the test bone profiles and the training bone profiles.

The procedure for segmenting a bone pattern is summarized in the following.

1. Smooth the image with a Gaussian filter.
2. Calculate the image partial derivatives with respect to the x and y dimensions by the following two masks:

$$\frac{\partial}{\partial x} = \begin{pmatrix} -1 & 0 & 1 \\ -1 & 0 & 1 \\ -1 & 0 & 1 \end{pmatrix} \text{ and } \frac{\partial}{\partial y} = \begin{pmatrix} -1 & -1 & -1 \\ 0 & 0 & 0 \\ 1 & 1 & 1 \end{pmatrix}.$$

3. Calculate the gradient magnitude by $$g = \sqrt{\left(\frac{\partial I}{\partial x}\right)^2 + \left(\frac{\partial I}{\partial y}\right)^2}$$

and the direction by $$\theta = \arctan\left(\frac{\partial I}{\partial y} \bigg/ \frac{\partial I}{\partial x}\right)$$

for each point of the image, where I represents the image.

Figure 4A:
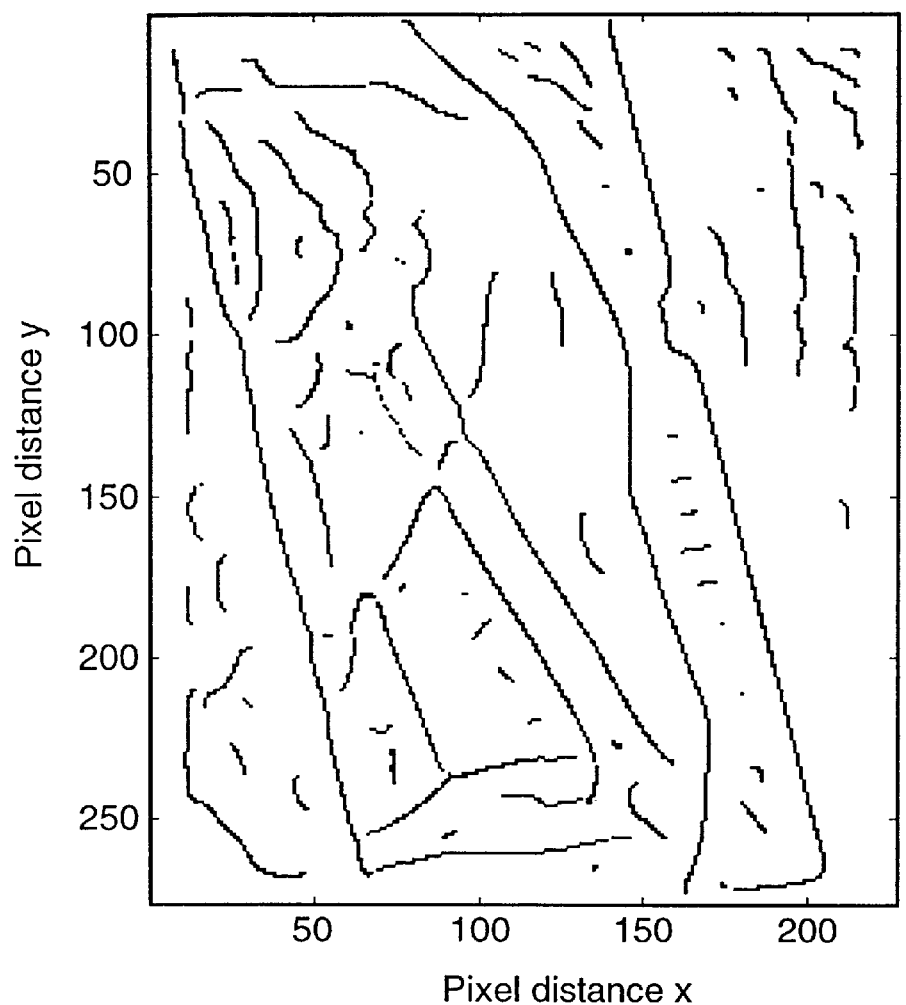
FIG. 4(a) is a diagrammatic view showing the candidate edge points of a humerus digital projection radiographic image.

4. Find the candidate edge points by finding the local gradient maximum along their gradient directions. FIG. 4(a) shows the candidate edge points of a humerus digital projection radiographic image.

Figure 4B:
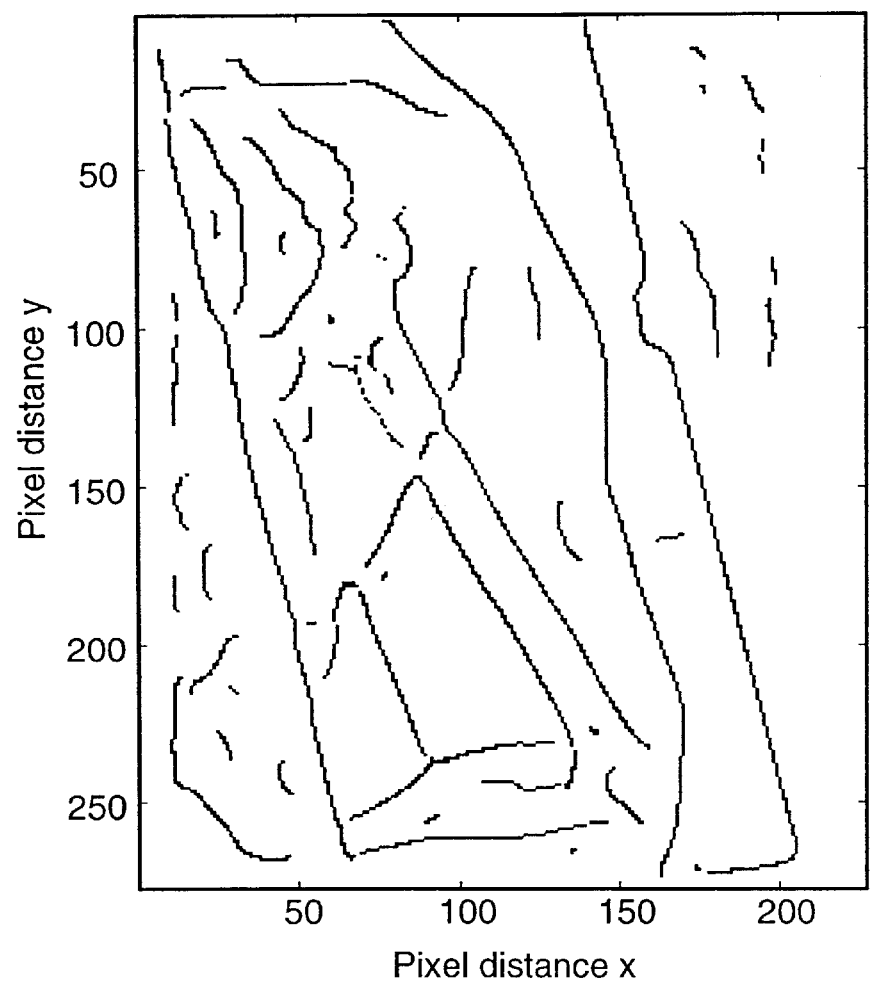
FIG. 4(b) is a diagrammatic view showing the edge points found in a humerus image after thresholding the gradient magnitude at $2.0 \times 10^3$.

5. For each candidate edge point, if its gradient magnitude is greater than a predetermined threshold, save it as the edge point. FIG. 4(b) shows the edge points after thresholding the gradient magnitude at $2.0 \times 10^3$.

6. For each edge point, generate a line along the gradient direction with a length of l, where l can be selected according to the length of the bone. For example, this line length is set to be l=4.5 cm for humerus images in our database. The length of this line is set to be 25 pixel units for a digital projection radiographic image with the resolution of 171 microns/pixel.

7. On that line, search for another edge point in each direction. To reduce the noise effects, starts the search at the middle point of that line segment and go towards the ending edge point.

8. After detecting an "ending" edge point, identify the line that connects the starting nd ending edge points. Suppose there are n pixel points on this line. Each pixel value n this line is determined by bilinear interpolation. Denote the profile vector for this line to be $P(1, \ldots, n)$.

9. Accept this ending edge point as a bone edge point if the following shape constraint conditions of the bone profile are satisfied: the maximum gradient of the profile is greater than a threshold value $g_{max}$ and the minimum gradient of the profile is less than a threshold value $g_{min}$.

10. If the above criteria are satisfied, save the edge points as the potential bone edge points, and save the profile vector $P(1, \ldots n)$ on the line connecting the pair of potential bone edge points.

Figure 4C:
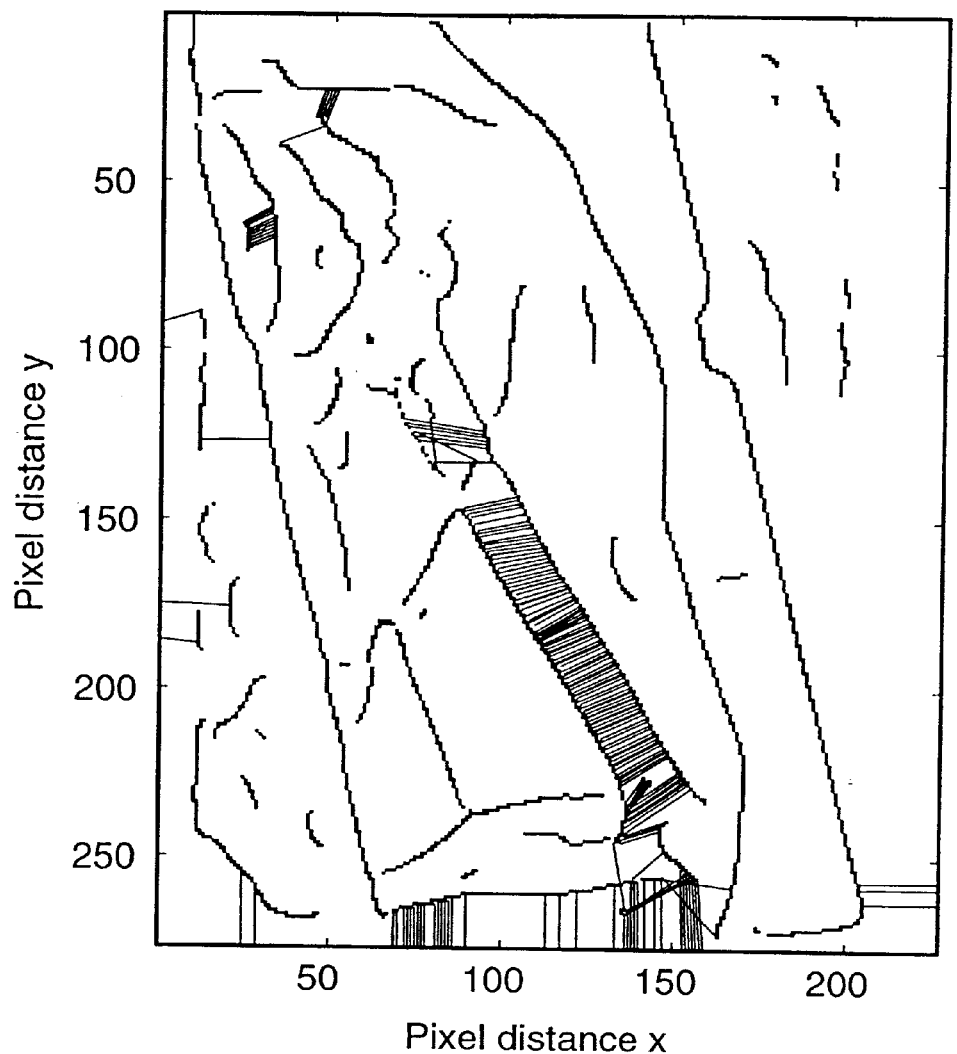
FIG. 4(c) is a diagrammatic view showing the potential bone edge points and the lines that connect the pair of potential bone edge points.

FIG. 4(c) shows the potential bone edge points and the lines that connect the pair of potential bone edge points. Then the profiles of these potential bone edge points are sent to the bone classifier, that is, the scatter measurement as shown in Section Locating cylindrical bones.

EXAMPLES (1) Training Set

Figure 5A:
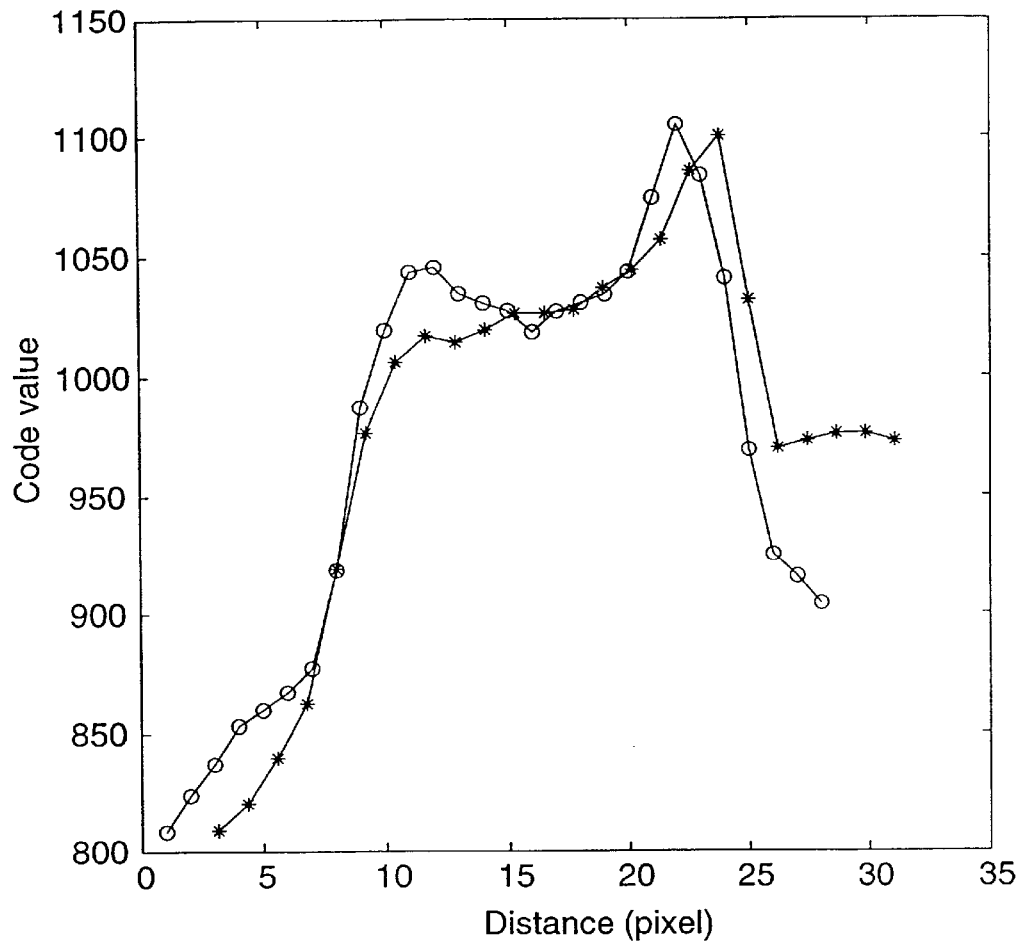
FIG. 5(a) is a graphical view showing the horizontally and vertically registered representative training bone profiles based on a basis profile, which is the profile with the circles on it.
Figure 5B:
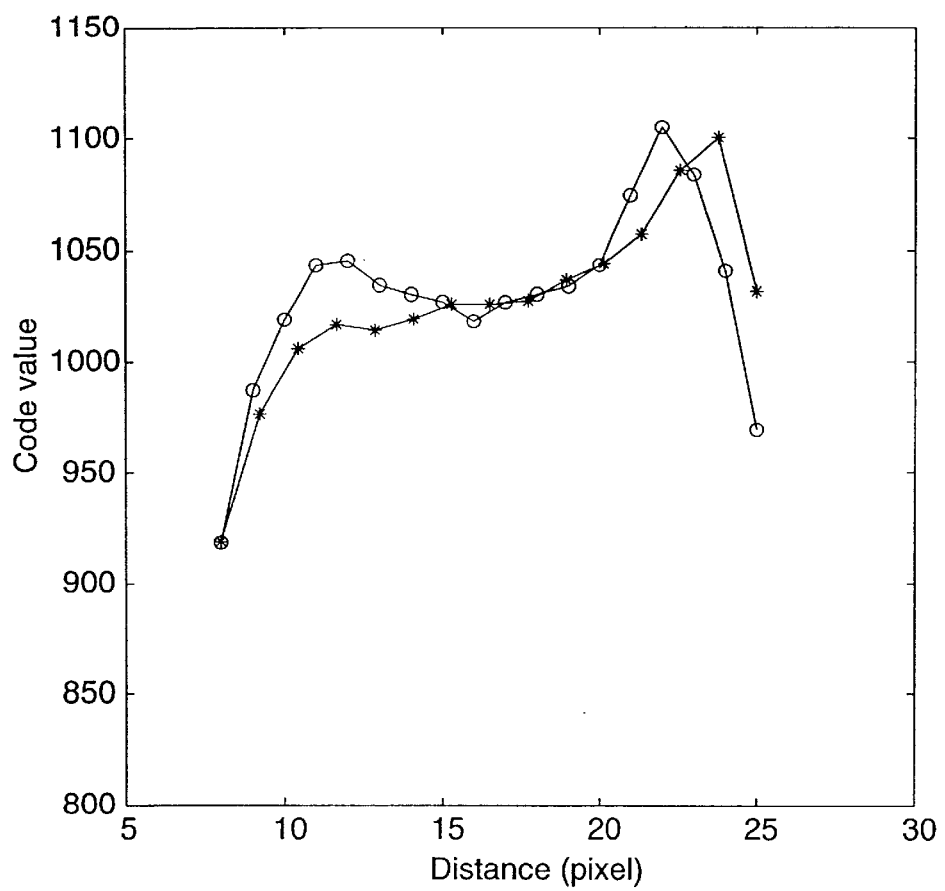
FIG. 5(b) is a graphical view showing the interpolated representative training bone profiles after the points beyond the maximum and minimum gradient points are truncated.
Figure 5C:
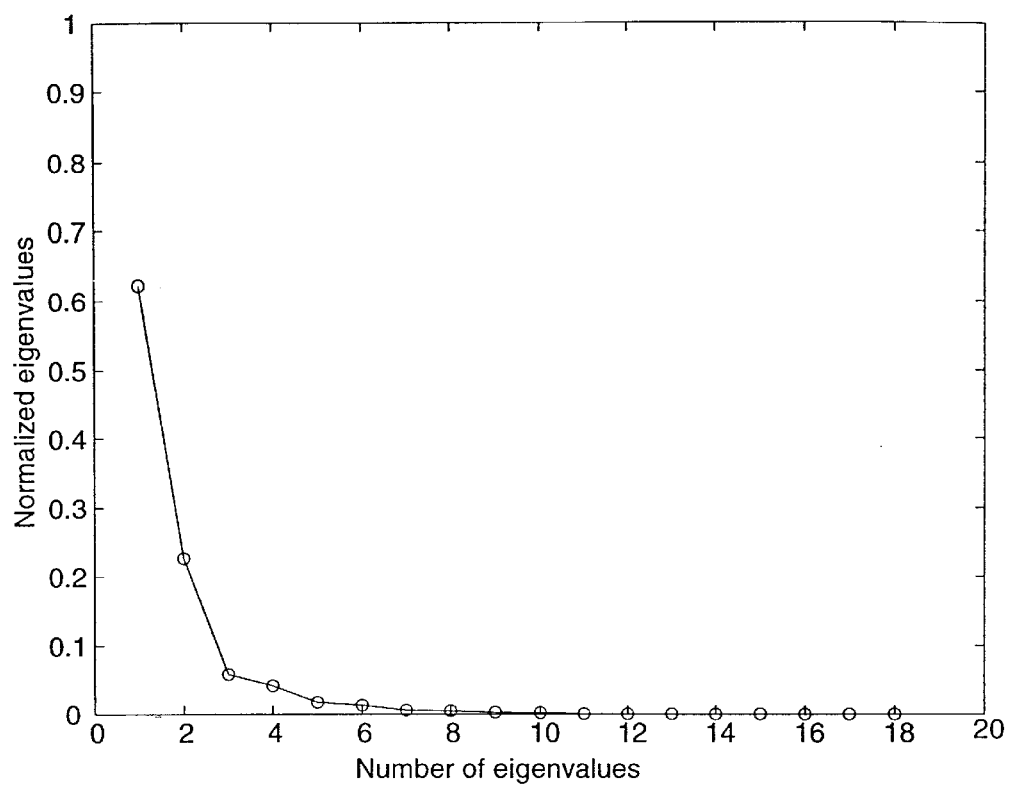
FIG. 5(c) is a graphical view showing the eigenvalues (normalized) obtained from the covariance matrix of 312 training bone profiles.

A set of 26 adult AP humerus images were selected from which 312 bone profiles were extracted as training bone profiles which included mirror profiles of the original profiles. The horizontally and vertically registered representative training bone profiles are shown in FIG. 5(a). The basis profile is the line with circles on it. Interpolated bone profiles after the points beyond the maximum and minimum gradient points are truncated are shown in FIG. 5(b). The training bone profiles P shown in equation (3) contain k=132 bone profiles and the number of sample points of each profile is n=18. FIG. 5(c) shows the eigenvalues of the covariance matrix of P. The numerical results indicate that the first 8 eigenvectors (eigenvalues) contain 99% of the energy of the training data, that is, $$\sum_{i=1}^{8} \lambda_i > 0.99 \sum_{i=1}^{18} \lambda_i.$$

Figure 5D:
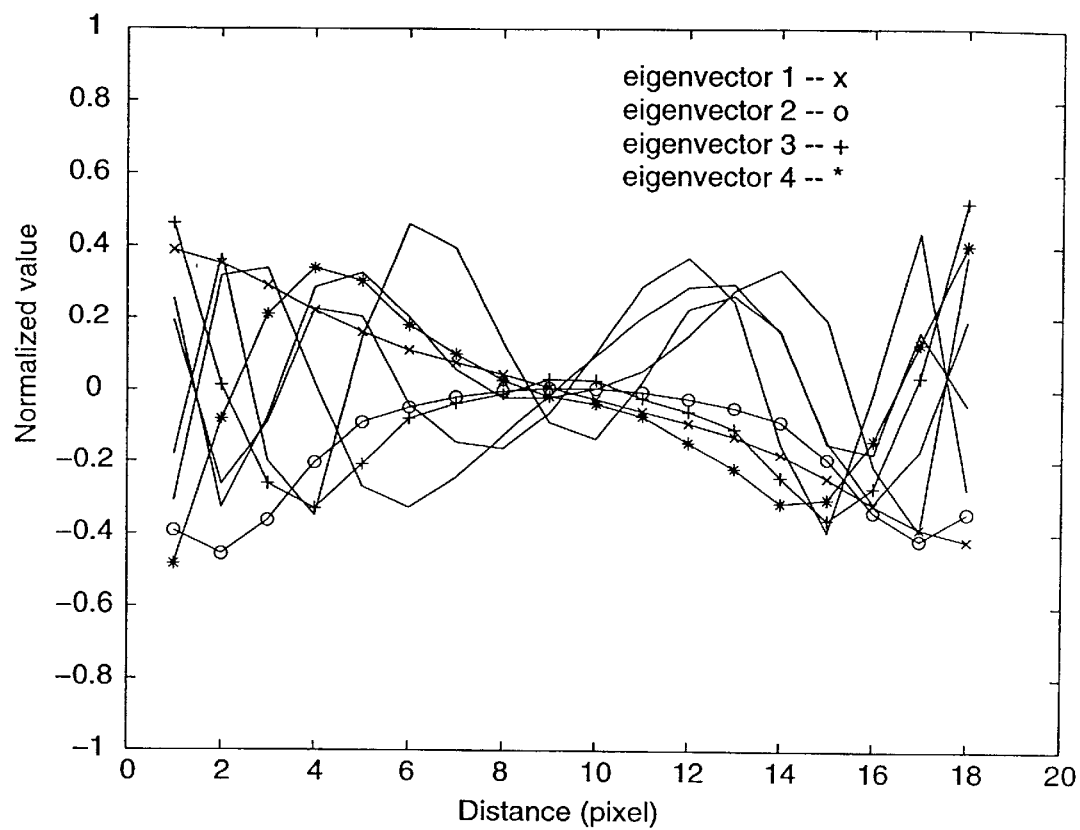
FIG. 5(d) is a graphical view showing the first 9 eigenvectors of the training bone profiles, where the first 4 eigenvectors are labeled as "-x-", "-o-", "-+-", and "-*-", respectively.

The first 9 eigenvectors of the bone profiles are shown in FIG. 5(d). The projection coefficients, after projecting 312 training bone profiles onto 8 eigenvectors in FIG. 5(d), are calculated. Therefore, 8 eigenvectors can be used to represent the bone profile that consists of 18 sample points. Hence, the dimension of the data in bone profiles is reduced. The projection coefficients obtained from eigenvectors of the bone profiles can be used to classify the bone and non-bone patterns.

(2) Test Set

Figure 6A:
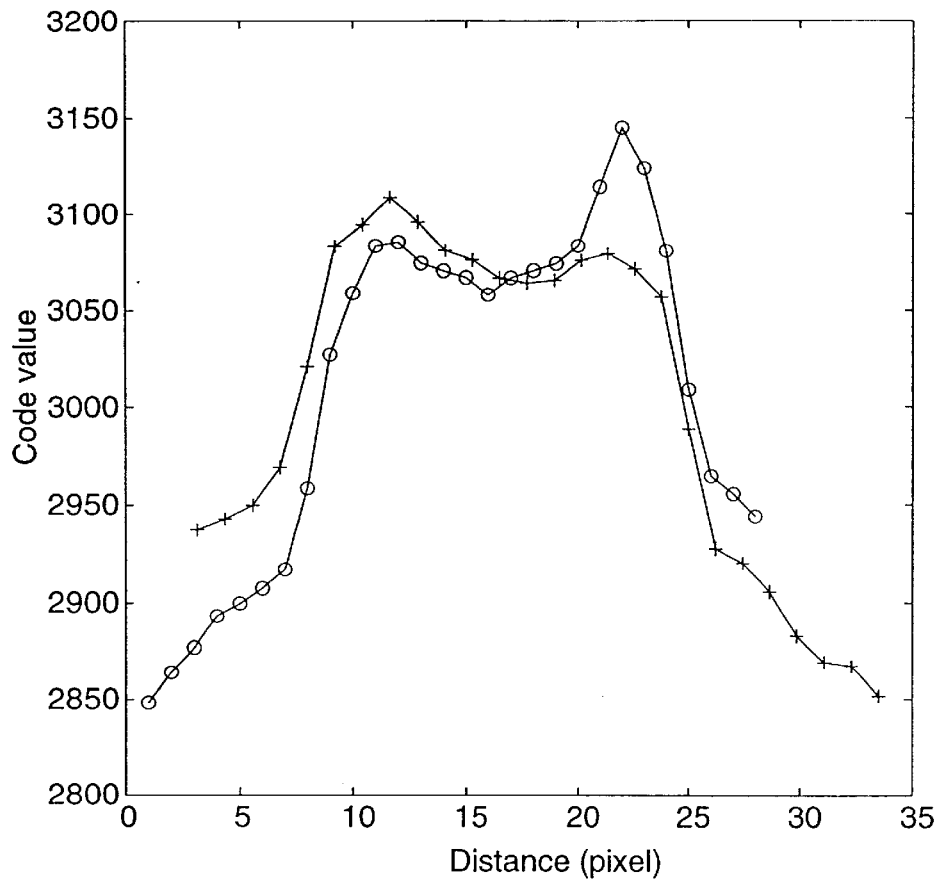
FIG. 6(a) is a graphical view showing the horizontally and vertically registered representative test bone profiles based on the same basis profile shown in FIG. 5(a).
Figure 6B:
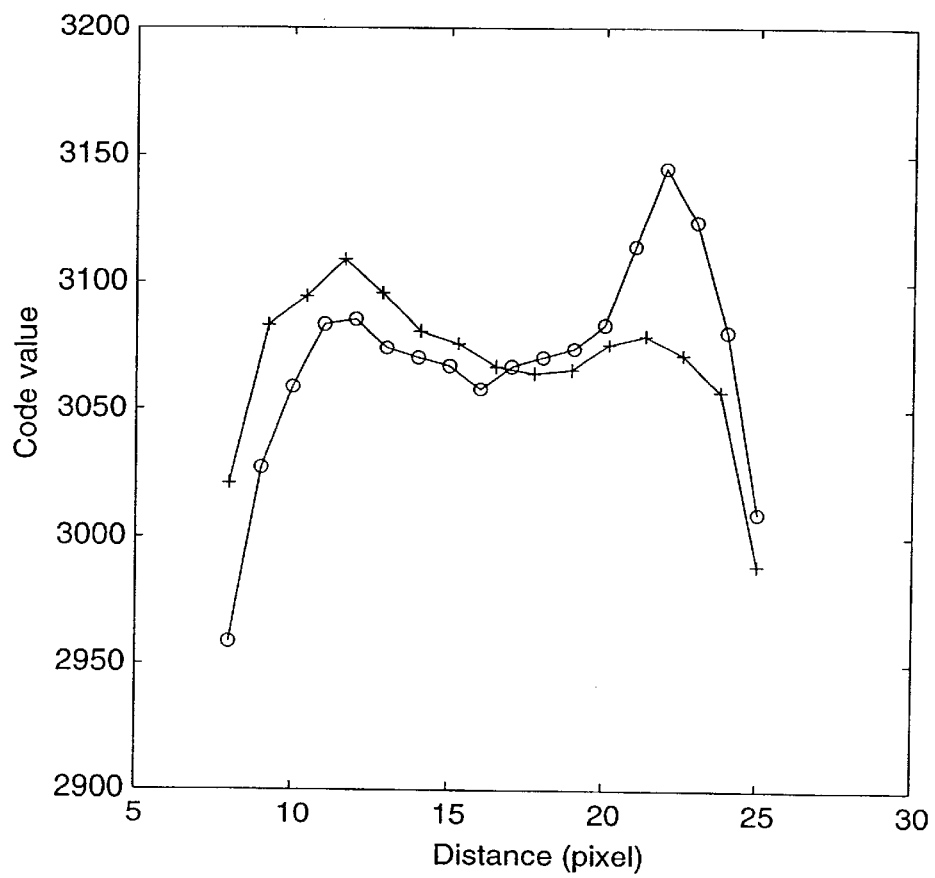
FIG. 6(b) is a graphical view showing the interpolated representative test bone profiles after the points beyond the maximum and minimum gradient points are truncated.

A set of 156 bone profiles were extracted from 7 adult lateral projections and 3 pediatric humerus images. Similarly, these test bone profiles included the mirror image profiles. Based on the same basis bone profile from the training set shown in FIG. 5(a), the horizontally and vertically registered representative test bone profiles are shown in FIG. 6(a). The interpolated test bone profiles after the points beyond the maximum and minimum gradient points are truncated and are shown in FIG. 6(b).

Figure 6C:
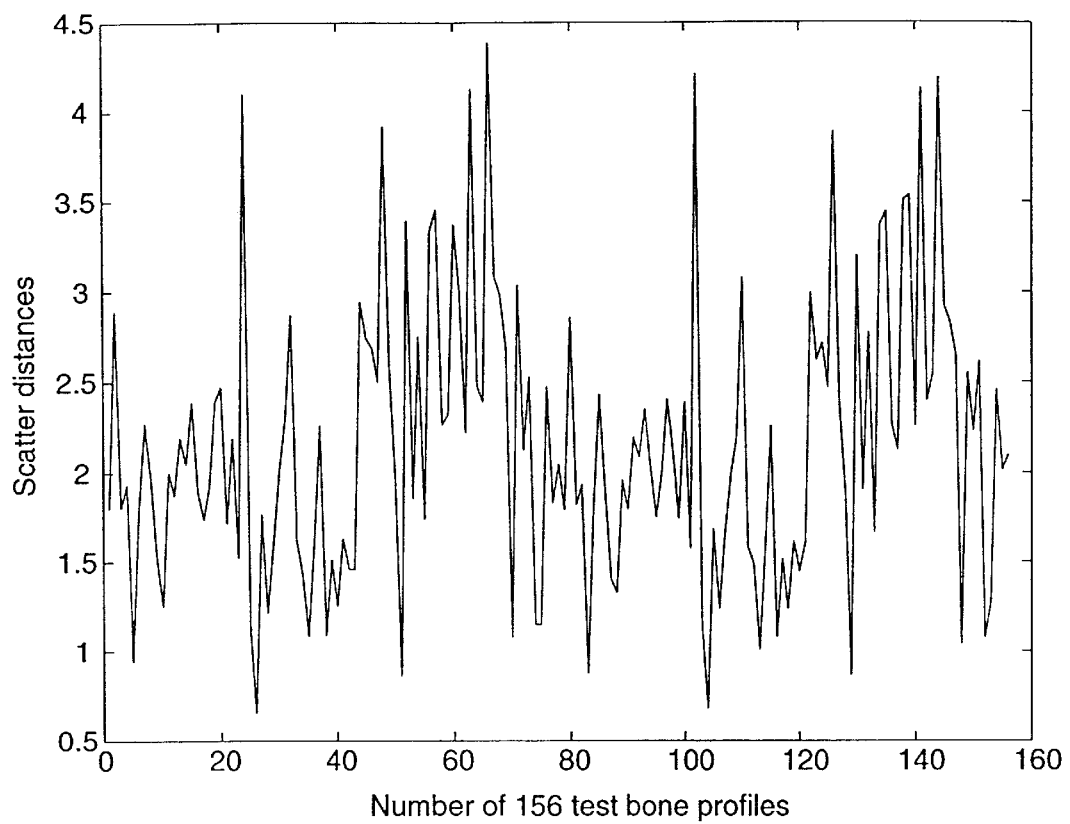
FIG. 6(c) is a graphical view showing the scatter measurement distances of 156 test bone profiles when using 8 eigenvectors.
Figure 6D:
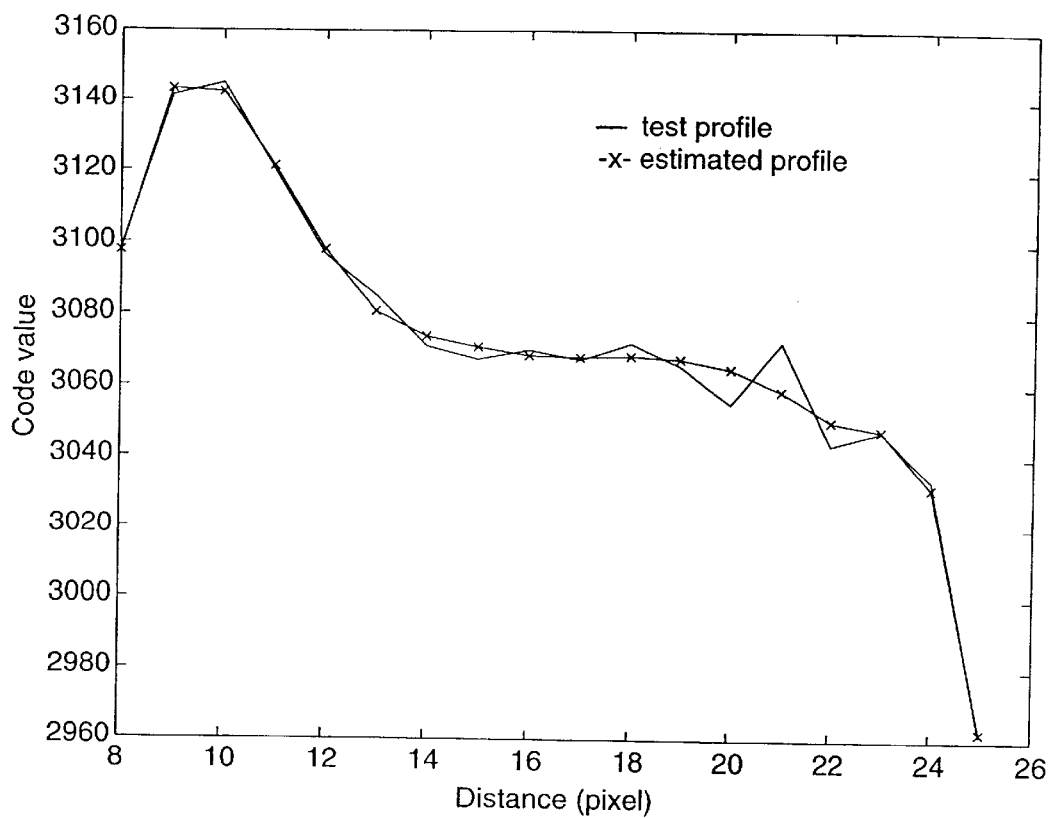
FIG. 6(d) is a graphical view of a test profile versus the corresponding estimated profile using 8 eigenvectors when the scatter distance is maximum (i.e., the worst estimated case).
Figure 6E:
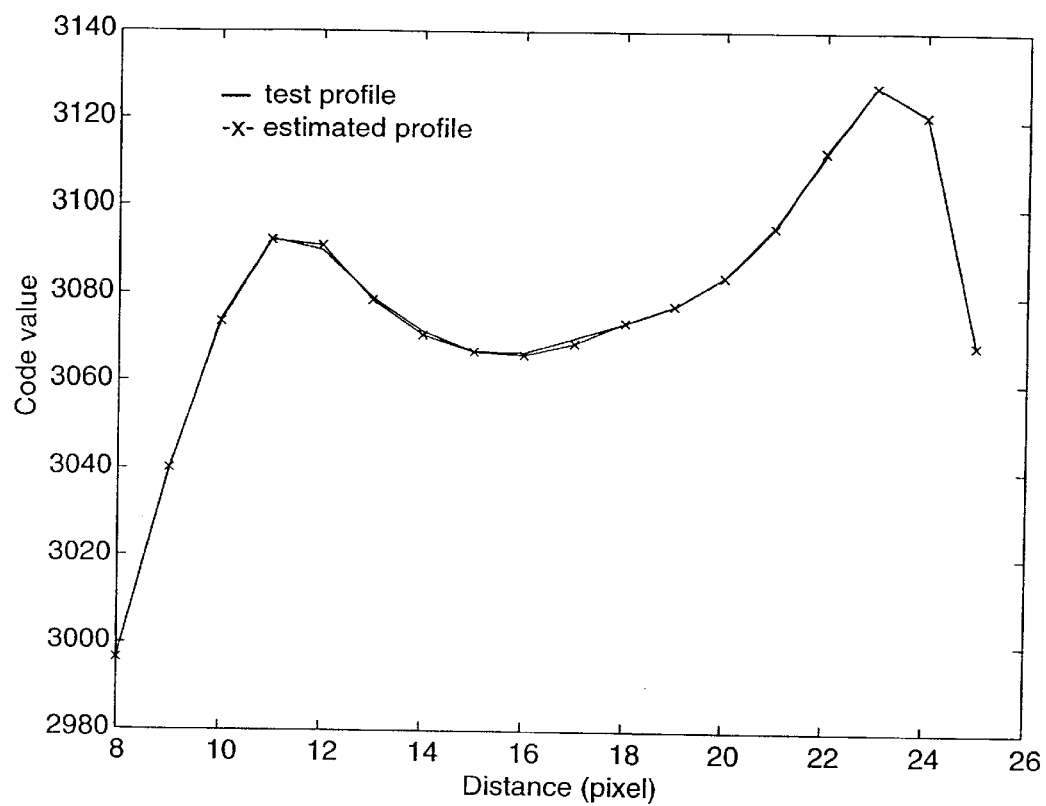
FIG. 6(e) is a graphical view showing a test profile versus its estimated profile using 8 eigenvectors when the scatter distance is minimum (i.e., the best estimated case).

The projection coefficients, after projecting 156 test bone profiles onto 8 eigenvectors of FIG. 5(d), were calculated. Next the scatter distance measurement was obtained using equation (5). These distances are shown in FIG. 6(c). The number of distances that are less than 3 is 136 (out of 156). This means that the correct classification rate is 88%. FIG. 6(d) shows the original bone test profile versus the estimated bone profile using 8 eigenvectors when the scatter distance is maximum (the worst estimated case), and FIG. 6(e) shows when the scatter distance is minimum (the best estimated case).

Figure 6F:
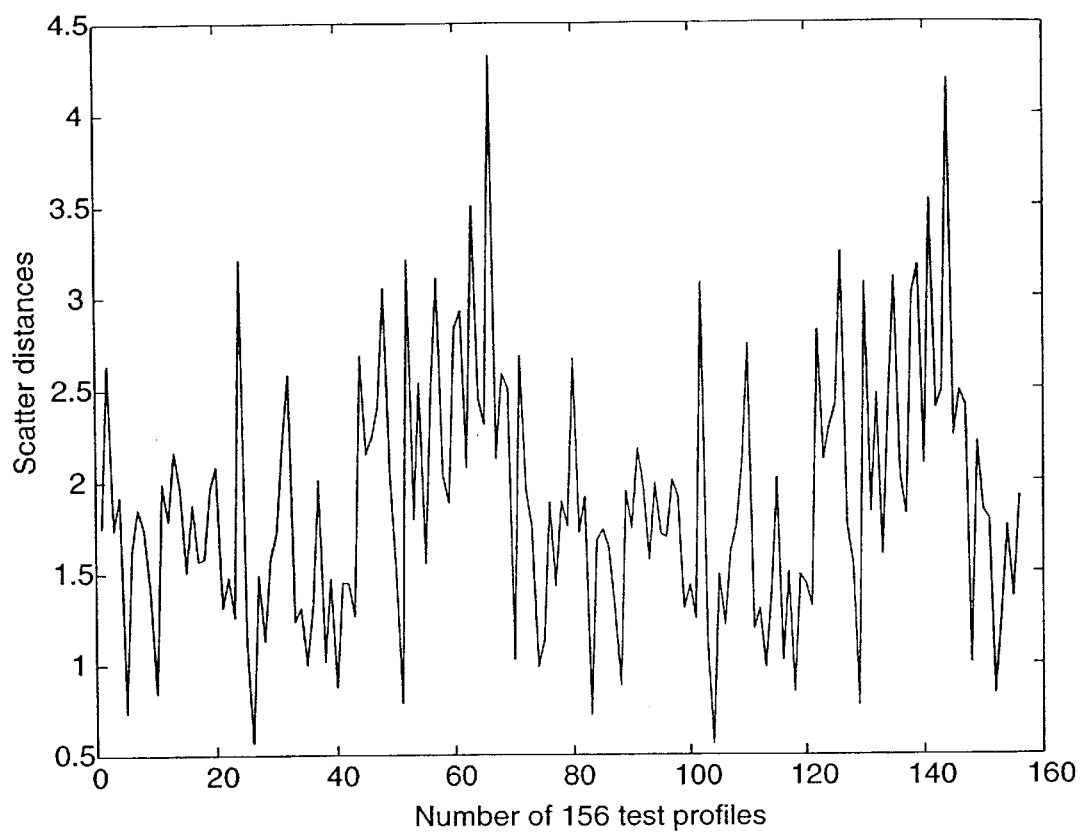
FIG. 6(f) is a graphical view showing the scatter measurement distances of 156 test bone profiles when using 6 eigenvectors.
Figure 6G:
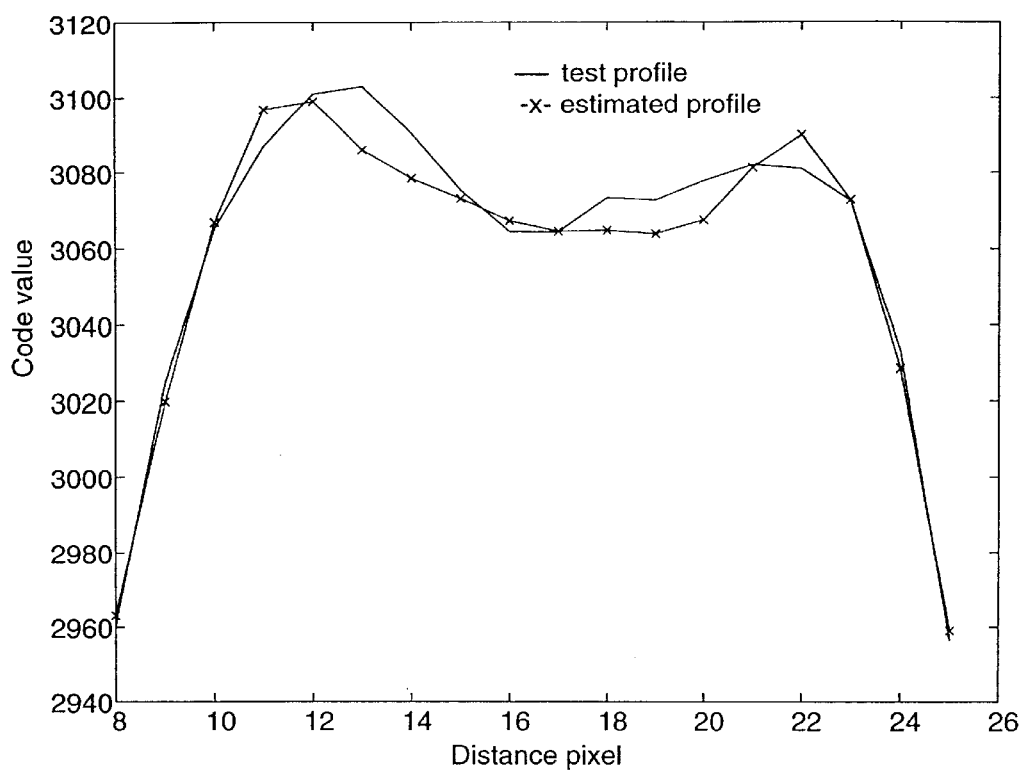
FIG. 6(g) is a graphical view of a test profile versus the corresponding estimated profile using 6 eigenvectors when the scatter distance is maximum (i.e., the worst estimated case).
Figure 6H:
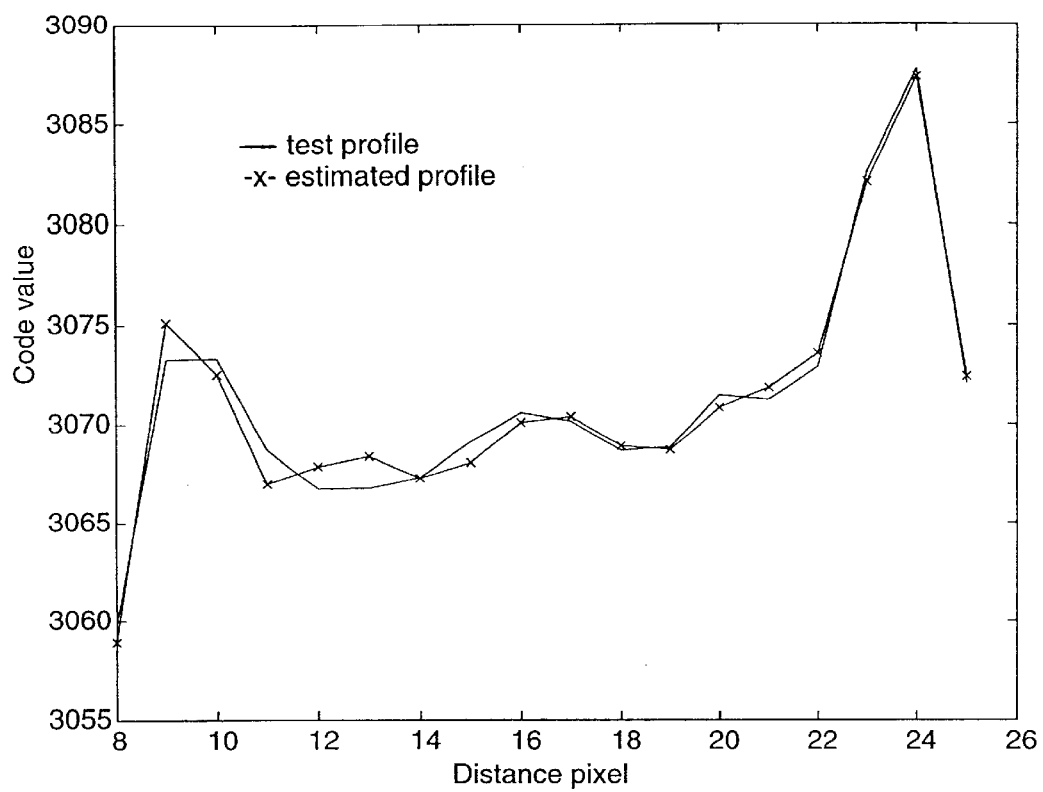
FIG. 6(h) is a graphical view showing a test profile versus its estimated profile using 6 eigenvectors when the scatter distance is minimum (i.e., the best estimated case).

FIG. 6(f) shows the scatter distances when the first 6 eigenvectors are used. The number of these distances that are less than 3 is 142 (out of 156). For this case the correct classifying rate is 91%. The worst and best fitting cases of the bone test profiles using 6 eigenvectors are shown in FIGS. 6(g) and 6(h). The fewer eigenvectors that are used reduces the noise level and the classification rate is increased. There is a trade off between the classification rate and the degree of approximation of the test bone profile. In this case, the sum of first 6 eigenvalues is 0.98 which indicates a good approximation.

(3) From Bone Regions to the Tone Scale Curve

Figure 7:
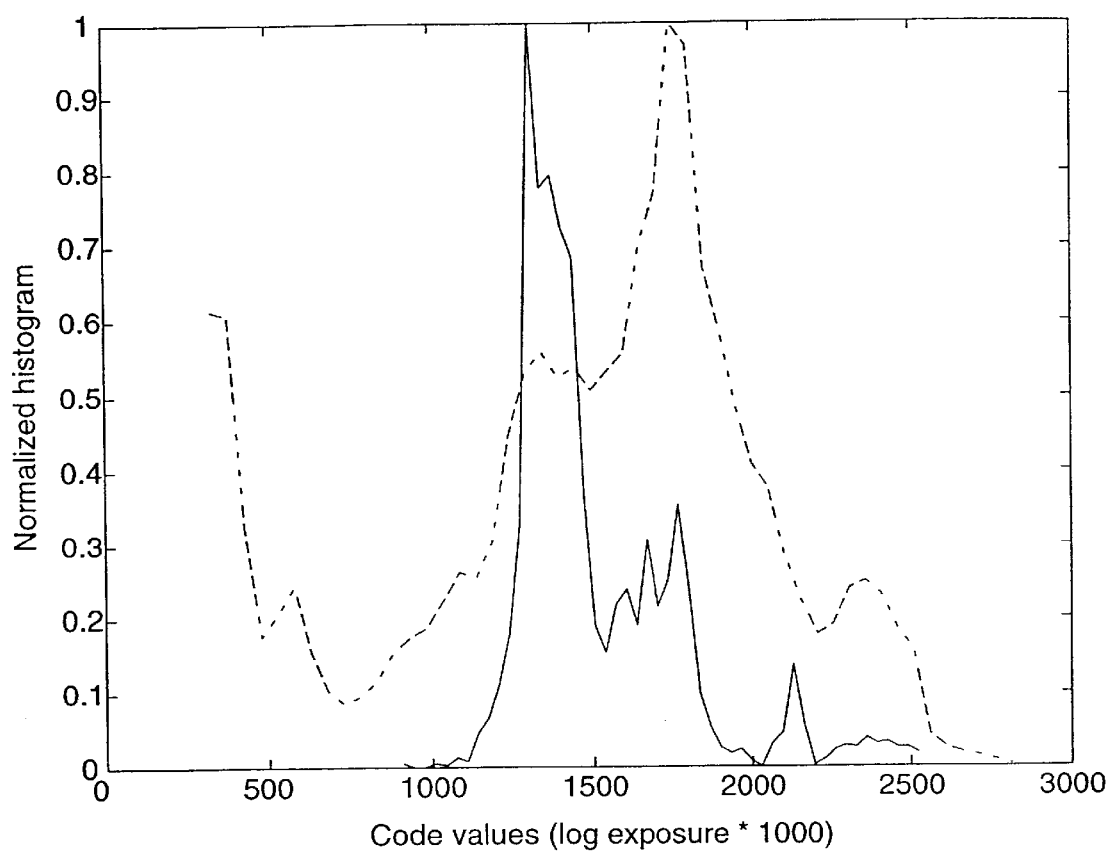
FIG. 7 is a graphical view showing the image-pattern histogram (obtained by the code values of the lines connecting the detected pairs of the bone edge points), the solid line, and the code-value histogram (obtained from the whole image), the dashed line, for a humerus digital projection radiographic image.

For the purpose of constructing the tone scale curve, the histogram was formed of the pixel points that fall on the lines connecting the valid pair of bone edge points. This histogram represents the code value distribution of the cylindrical bone region, which are bone structures in the extremity image. This histogram is the image-pattern histogram. FIG. 7 shows the image-pattern histogram (the solid line) and the code-value histogram of the entire image (the dashed line) for a single humerus image. From this figure, it is observed that most of the code values for the bone regions occur between 1200 to 2000, while the code values of the entire image span the range from 200 to 3000.

From the image-pattern histogram, four points are identified in the input image code value range, that can form the input for the construction of a visually optimized tone scale (U.S. Pat. No. 5,633,511, issued May 27, 1997, to inventors H.-C Lee et al.). These four points are called the far-left, the left, the right, and the far-right points. The code values between the left point and the right point correspond to the sub-range of the input code values. This sub-range corresponds to the most important body parts that are examined. In the case of extremity image, this sub-range corresponds to cylindrical bone patterns. The far-left and far-right points are used to roll off both ends (the toe and the shoulder) of the tone scale curve. This will prevent the tone scale curve from producing a hard clipping in the displayed image.

(4) From Bone Regions to Bone Mineral Density Measurements

One of the computer aided diagnosis applications in detecting bone disease, such as osteoporosis, is based on analyzing the bone morphology in x-ray images. For example, in the total body study, the locations of arms and legs are important. In the peripheral skeleton scanning study, the location of the forearm, or the location of the fingers, are crucial. In this section, an example is shown of locating fingers for purposes of measuring bone mineral density. In radiographic absorptiometry, the bone mineral density is measured by correlating the optical density of the region of phalanges of the hand in the radiograph and the density of a bone-like wedge that is imaged with the hand. Therefore, the location of phalanges of the hand needs to be obtained. The bone mineral content (BMC) is derived by multiplying the mean BMD by the phalange area:

$$BMC = BMD \times \text{Area}.$$

Therefore, the area of the region of phalanges of the hand also needs to be calculated.

Figure 8A:
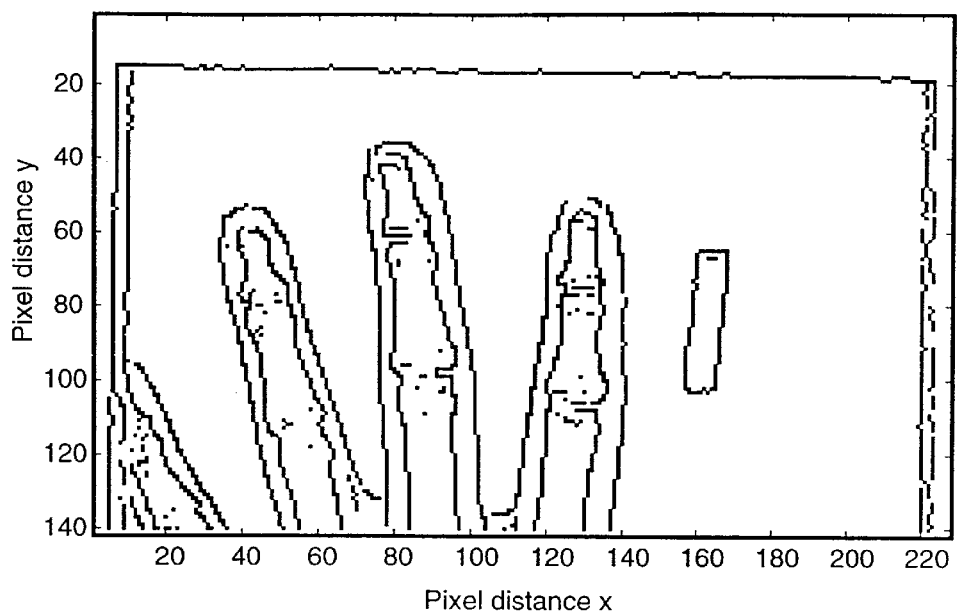
FIG. 8(a) is a diagrammatic view showing the edge points found in a digital projection radiographic image of a hand.
Figure 8B:
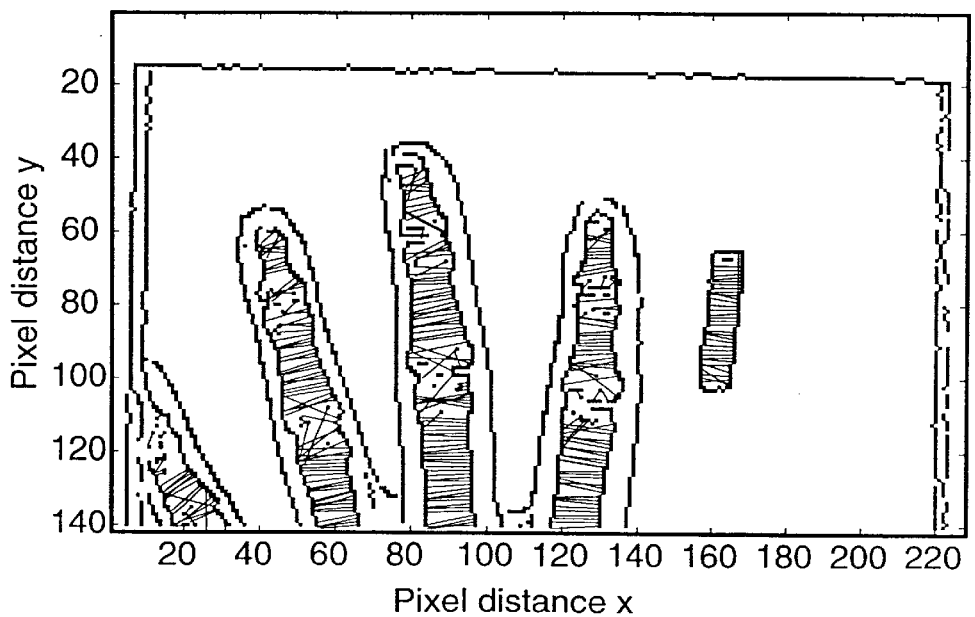
FIG. 8(b) is a diagrammatic view showing the potential bone edge points and the lines that connect the pair of potential bone edge points.

An example of locating finger bones in a hand image is shown in this section. The edge points in a hand digital radiographic image is shown in FIG. 8(a). Observe that the finger bones, the skin lines, and the collimation edges are all found at this stage. Then the bone pattern segmentation algorithm (see Section (5), Bone pattern segmentation), which is based on the constraints of the shape of the bone profile, is applied to the resultant image in FIG. 8(a). The potential bone edge points and the lines connecting the pair of potential bone edge points are shown in FIG. 8(b). We can observe that most of the finger bone points are correctly located. The wedge in the image is also detected. This can be classified as non-bone patterns by the eigenvector analysis method described in Section (3), Scatter measurement. In another hand, the location of the wedge is also needed to calculate the bone mineral density from the density of the wedge that is imaged with the hand. Hence, the location of the wedge is saved. Usually, the mineral density is measured in the middle finger at three phalanges. A simple stripe algorithm can be applied to locate three phalanges separately.

The invention has been described in detail with particular reference to certain preferred embodiments thereof, but it will be understood that variations and modifications can be effected within the spirit and scope of the invention.

PARTS LIST 30 image acquisition system
32 image pattern filter
34 image display 300 digital computer
310 memory
312 input device
314 display
316 central processing unit
318 output device
320 control/data bus
322 transportable storage medium drive

What is claimed is:

1. A method of automatically locating cylindrical bones comprising:

providing a digital image having cylindrical bones;

applying a bone edge filter to said digital image;

searching for a pair of candidate starting and ending bone edge points;

determining a profile vector of the line connecting the starting and the ending edge points; applying an eigenvector classifier; and saving the classified bone edge points wherein said searching includes:

detecting a starting bone edge point;

generating a line along the gradient direction;

searching for another edge point on the said line in both directions;

determining a profile vector of the line connecting the starting and the ending edge points;

checking the local maxima conditions, that is, for a valid pair of bone edge points, the maximum gradient of the profile is greater than a threshold value $g_{max}$; and checking the local minima conditions, that is, for a valid pair of bone edge points, the minimum gradient of the profile is less than a threshold value $g_{min}$.

2. A method of claim 1 wherein said eigenvector classifier is designed by:

providing a set of digital images having cylindrical bones;

determining eigenvector representation of cylindrical bone profiles;

determining a scatter measurement; and determining bone profile registration.

3. The method of claim 2 wherein said bone profile registration determining includes:

determining horizontal registering;

determining vertical registering; and determining interpolation.

4. The method of claim 1 including inputting a set of training images; generating the eigenvector representation of the characteristic profiles of each of said set of training images and using all the data from the generating in applying the eigenvector classifier.

* * * * *